United States Patent [19]

Griffin

[11] Patent Number: 4,886,655

[45] Date of Patent: Dec. 12, 1989

[54] METHOD OF DETECTING INFECTION OR IMMUNITY IN RUMINANTS

[75] Inventor: John F. T. Griffin, Dunedin, New Zealand

[73] Assignee: The University of Otago, Dunedin, New Zealand

[21] Appl. No.: 935,896

[22] Filed: Nov. 28, 1986

[30] Foreign Application Priority Data

Dec. 2, 1985 [NZ] New Zealand .................. 214400

[51] Int. Cl.$^4$ ............................................. G01N 1/00
[52] U.S. Cl. ..................................... 424/2; 435/4; 435/13; 435/29; 436/501
[58] Field of Search ............... 424/2; 435/4, 13, 29; 436/501

[56] References Cited

U.S. PATENT DOCUMENTS 4,610,878 9/1986 Wilson et al. ........................ 435/7

FOREIGN PATENT DOCUMENTS 0067646 of 1982 European Pat. Off.
2149105 A of 1985 United Kingdom.

OTHER PUBLICATIONS

Clinical Hematology, Wintrobe, et al. (editors), Lea & Febiger Pub., Phila., 1974, pp. 123–134.
Biological Abstracts, vol. 62, No. 8, (1976):43187.
Muscoplat et al., "Development of Specific in Vitro..", Am J Vet Res., 36, No. 4., (Apr. 1975), 395–398.
Muscoplat et al., "Development of Specific Lymphocyte...", Am J Vet Res, 36, No. 8, (Aug. 1975), pp. 1167–1171.
Buergetl et al., "In Vitro Lymphocyte Transformation...", Am J Vet Res, 39, No. 4, (Apr. 1978), pp. 591–595.
Liberg, "The Fibrinogen Concentration...", Chem. Abstracts 52932h, vol. 90, (1979), p. 450.
Schattner et al., "Comparison of (2'-5')...", 123745c Chem. Abstracts, vol. 98, 1983, p. 321.
Seawright et al., "Automation of the Enzyme...", Chem. Abstracts 111255t, 95, 1981, p. 322.
Powanda, et al., "Phagocytosis and the Metabolic...", Chem. Abstracts 126284p, vol. 92, 1980, p. 474.

Primary Examiner—Robert J. Warden
Assistant Examiner—Stephen C. Wieder
Attorney, Agent, or Firm—Nixon & Vanderhye

[57] ABSTRACT

The invention provides a method of detecting infection and/or immunity in ruminants. The method includes the steps of conducting an assay of mononuclear cell function and measuring a parameter of inflammation of a sample of blood from a ruminant, and comparing the results obtained with a predetermined database. The method of the invention is particularly suitable for detecting tuberculosis in deer.

13 Claims, 3 Drawing Sheets

UNKNOWN STATUS

Hb - Haemoglobin
NAN - Neutrophil Numbers
Lym - Lymphocyte Numbers
Fib - Fibrinogen Levels
TRB - Transformation with Myco bovis
%N - Neutrophil percent

METHOD OF DETECTING INFECTION OR IMMUNITY IN RUMINANTS

This invention relates to a method of detecting infection in ruminants. More particularly, it relates to a method of detecting various diseases in a ruminant by testing samples of blood obtained from the ruminant.

The central role of ruminants in the primary produce sector highlights the need to safeguard these animals from disease. The control of these diseases is vital to the profitability of this form of industry. Accordingly, the detection of infection in a herd of animals in order to allow infected animals to be isolated and/or culled to safeguard the remainder of the herd is of great importance.

The central physiological mechanism involved in protection against infection is the immune system. Exposure of an individual to a virulent organism activates the immune system to produce antibodies or activated lymphocytes (T-cells) which act to neutralize or kill the offending organism and cause its elimination. However, although antibody production is effective to control acute bacterial infection caused by toxin-producing bacteria, it has no direct impact on chronic bacterial infection by organisms such as those which cause tuberculosis. Cell mediated immunity (CMI), produced by specific T-cells controls infection by walling off the organisms within a cellular lesion (granuloma). A residual memory of the organism remains after resolution of the infection.

Immune parameters have been widely used in a veterinary medicine to identify animals which have mounted an immune response following exposure to infection. In particular, measurement of CMI by intradermal cervical skin testing (CT) has been applied widely for the identification of tuberculosis-infected humans and cattle for the past fifty years. This test, although having a number of advantages, also possesses a number of limitations. The limitations of particular concern are as follows: the test lacks the ability to detect some infected animals within a herd due to undetectable immune response (FALSE (−) reactors); if a bovine tuberculin alone is used in the CT it will produce reactions in TB uninfected animals exposed to nonvirulent organisms e.g. M.avium (FALSE (+) reactors); as the incidence of TB infected herds decreases, the number of non-visible lesion (NVL) reactors found may become significant; and a relatively long interval is necessary between herd tests (up to 3 months) as skin testing causes a suppression of reactivity for up to 60 days post testing. A further concern in relation to use of the CT test as a means of identifying infection is that this test precludes the possibility of vaccination of the animals as a positive skin test will result irrespective of whether the animal is infected or immune.

Of the above, the failure of the CT test to detect heavily infected animals which produce an undetectable immune response, constitute a major hazard to the industry in that this leaves the infected animals in the herd to infect other previously healthy animals.

It is an object of the present invention to go some way towards overcoming the above disadvantages or at least to provide the public with a useful choice.

Accordingly, in one aspect the present invention may broadly be said to consist in a method of detecting infection in a ruminant comprising (a) obtaining a sample of blood from said ruminant (b) conducting an assay of mononuclear cell function;

(c) measuring a parameter of inflammation of said sample; and (d) comparing the results obtained in steps (b) and (c) with a predetermined database to establish the infective status of said ruminant.

The term "infection" as used herein means the presence of microorganisms under conditions which produce replication and evoke a host response, designated a lesion.

Conveniently the assay conducted in step (b) tests for the transformation of T-cells or for lymphokines produced by activated T-cells.

In preferred embodiments of the invention the parameter of inflammation tested for is a macrophage cell count, a neutrophil cell count, the plasma viscosity of the sample, or a determination of the level of inflammatory plasma proteins in the sample.

In a further aspect, the invention may be said to consist in a method of differentiating between infection and immunity in a ruminant comprising:

(a) obtaining a first sample of blood from said ruminant;

(b) conducting an assay of mononuclear cell function in said first sample;

(c) measuring a parameter of inflammation of said first sample;

(d) comparing the results obtained in steps (b) and (c) with a predetermined database to determine a presumptive diagnosis of the infective status of said ruminant;

(e) if the presumptive diagnosis suggests that the ruminant is infected, waiting for a period of time to elapse which is sufficient to allow for confirmation as to whether the infection is becoming established or resolved to be made;

(f) obtaining a second sample of blood from said ruminant;

(g) repeating steps (b), (c) and (d) above for said second sample in order to determine a confirmatory diagnosis of the infective status of said ruminant; and (h) comparing the presumptive infective status and the confirmatory infective status in order to determine whether said infection is becoming established or resolved.

Although the invention is as broadly described above, it will be appreciated by those persons skilled in the art that it is not limited thereto and that it also includes embodiments of which the following gives examples, In particular, aspects of the invention will be more clearly understood by having reference to the accompanying drawings wherein FIG. 1 is a representation of the cell interactions in the immunological response.

The present invention consists in detecting the presence or absence of infection in a ruminant by analysing the blood of the ruminant. In particular, the invention relates to a method of analysing a sample of blood in order to establish the presence or absence of factors indicative of infection.

Although the invention will be more particularly described in relation to the detection of tuberculosis (TB) in deer, it will be appreciated that TB and deer are but one example of a chronic infection of a ruminant to which the method has application. The method also has application to other ruminants such as cattle, sheep and goats, and to other infections of such ruminants.

The first step of the method involves the step of obtaining a sample of blood from a ruminant. This can be achieved by any method known in the art appropriate for this purpose. Conveniently, a 20ml blood sample is extracted from the ruminant by use of a syringe.

Figure 1:
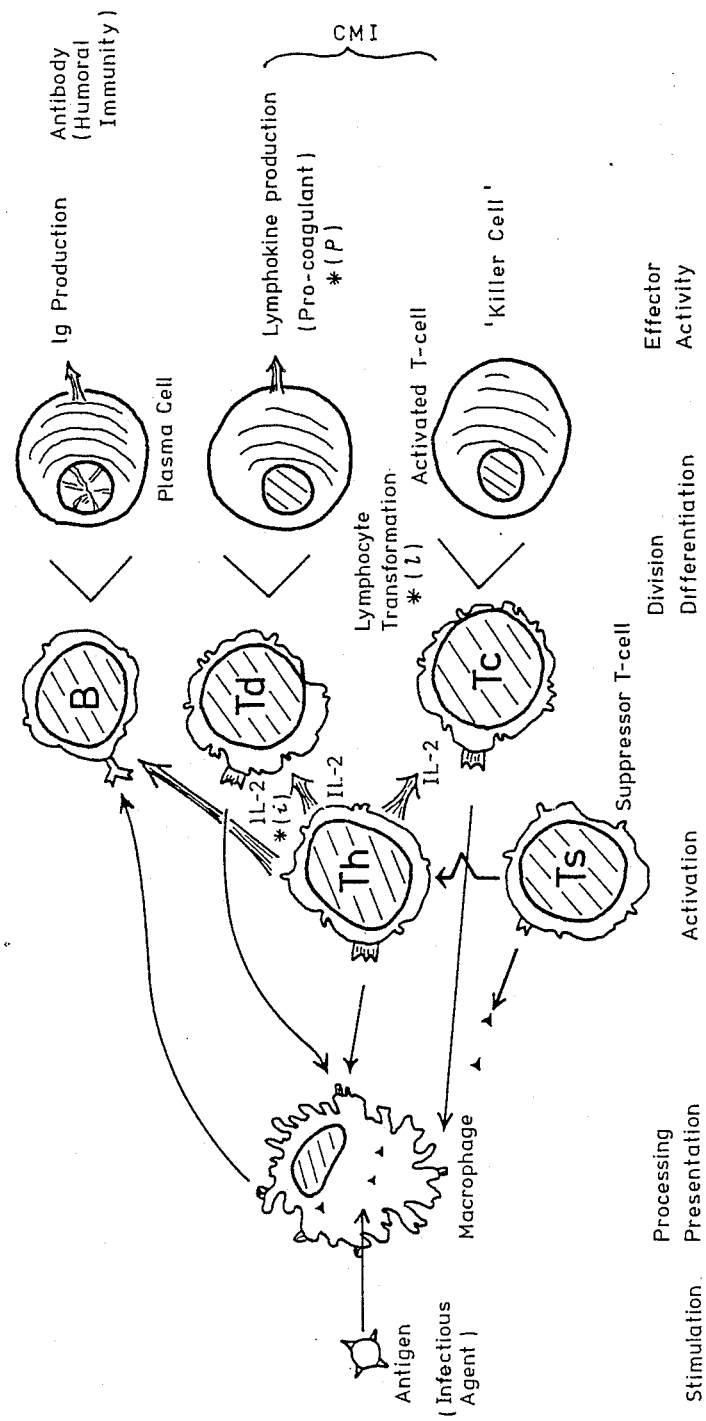

In the second step of the method according to the invention, the sample of blood is assayed to determine the mononuclear cell function. Mononuclear cells are an integral part of the immune system response to invading organism, the basic mechanisms of which response are set out in FIG. 1. Examples of preferred sites at which such mononuclear cell assays may be performed are shown in FIG. 1, these sites being designated (l), (i), (p) respectively.

The assay at site (l) is commonly known as lymphocyte transformation (LT) assay and monitors the specific activation of a subpopulation of T-lymphocytes (the Td cells). More specifically this assay involves the exposure of the mononuclear cells obtained from a blood sample to an antigen followed by the cultivation of the monovated nuclear cells in the presence of radiolabelled nucleotides, for example tritiated thymidine. The uptake of the radiolabelled nucleotides measures the rate at which the T-cells replicate under the specific influence of the test antigen. This specificity of response is of particular importance to the determination of whether there is true infection or not.

The assay at site (i) involves a measurement of the lymphokine interleukin-2 (IL-2) produced by another sub-population of the T-lymphocytes, the Th cells. The blood sample is separated into blood cells and supernatant by, for example, centrifugation, and the supernatant retained. The amount of interleukin-2 produced is quantified by the ability of the culture supernatant to activate standard target cells. As IL-2 is produced at an early stage of the immune response, this assay allows an assessment of the stage to which the infection has progressed to be made.

The assay at site (p) also measures the activation of the Td cells. The cells when activated produce another lymphokine in the form of a special inflammation promoting factor called Pro-coagulant. The production of this factor activates inflammatory cells to stimulate the coagulation pathway and in particular the conversion of fibrinogen to fibrin. The amount of Pro-coagulant present is quantified by separating the cells from a blood sample, adding the cells to calcium free plasma and measuring the length of time it takes for the plasma to clot.

Other assays which may be used to measure mononuclear cell function also involve a quantification of lymphokine production by activated cells. Examples of such other assays include a determination of the level of production of tumor necrosis factor (TNF) or of interferon.

The above is a general description of the assays which may be used in the second step of the method. The details of these assays will be clearly understood by those persons skilled in the art.

The third step of the method according to the invention comprises measuring a parameter of inflammation of the blood sample. Examples of parameters which may usefully be measured are macrophage cell populations, neutrophil cell populations, plasma viscosity and the level of inflammatory plasma proteins such as fibrinogen or $\alpha$-2 globulins.

Although it is possible to use one such parameter in the method according to the invention, in preferred embodiments more than one parameter of inflammation is measured in order to reduce the possibility of error. For example, all four of the parameters exemplified above may be measured.

The cell populations in the blood sample can easily be measured by the use of an automated cell counter such as the Technicon Haematology Analyser H 6000/C. Such a machine quantifies the population of a particular cell by measuring the size of and light scattered by the cell as well as the enzyme content of the cell.

Plasma viscosity may also be determined by a machine for measuring this factor such as a Harkness Viscometer. This machine measures the viscosity of the plasma by measuring the flow rate of the sample through a capillary tube of a standard size at a controlled temperature.

Fibrinogen levels in the sample are measured by determining the time necessary for fibrin to form when thrombin is added to the sample.

The presence of $\alpha$-2 globulins in the sample may be measured using standard ELISA techniques.

The remaining step in the method comprises comparing the results of the assay of step (b) and the measurement of step (c) with a predetermined database in order to determine the infective status of the ruminant. The database is established by taking a large number of animals deemed to be normal and both assaying the mononuclear cell function and measuring each of the parameters of the blood sampled from the animals. The mean of the results obtained is then calculated together with the deviation from the mean in order to establish a reference distribution range.

Although the reference database is established using animals deemed to be normal, it will be understood that the mean and distribution range for each result will be augmented with, and if necessary, refined by data from animals whose infective status is subsequently confirmed by autopsy. Optimally, the database will only include data from animals whose infective status has been confirmed in this way.

An example of a database determined as above for deer is as given below as Table I.

TABLE 1

Results are expressed as counts per minute (Cpms.) following the incubation of $2 \times 10^5$ deer mononuclear cells with $0.5\mu$ Ci 3H - thymidine for the last 18 hours of a 144 hour culture period. Reference range, means and standard deviations derived from 205 mixed aged adult deer taken from Tb free properties without a history of skin test reactions. Reactor range taken from 145 Avian Reactor and 450 Bovine Reactor samples.

| CONTROL ANIMAL REFERENCE VALUES | | | |
|---|---|---|---|
| Avian PPD | Bovine PPD | Concanavalin A | Control |
| Mean 450* | 516 | 63,456 | 360 |
| Standard Deviation 135 | 203 | 20,154 | 163 |
| *Cpms. | | | |

| Cut Points for Classification | |
|---|---|
| Avian Reactor Transformation (Range 10-675)+ | Bovine Reactor Transformation (Range 10-774) |
| A1  10-100 | B1  10-100 |
| A2 101-200 | B2 101-200 |
| A3 201-300 | B3 201-300 |
| A4 301-400 | B4 301-400 |
| A5 401-500 | B5 401-500 |
| A6 501-600 | B6 501-600 |

TABLE 1-continued

| A7 601–700 | | | B7 601–700 B8 701–800 | |
| --- | --- | --- | --- | --- |
| +Cpms. × $10^2$ | | | | |
| Haematology Range (Weaners) | | | | |
| Fibrogen | 167–387 | (mg/dL) | Neutrophils | 26–65% |
| Plasma viscosity | 1003–1171 | (cp) | Neutrophils | 0.79–4.21 × $10^9$/L |
| Haemoglobin | 160–213 | (g/L) | Lymphocytes | 1.34–3.61 × $10^9$/L |

As can be seen from the above table, the animals are divided into classes A1–A6 or B1–B8 depending upon the results of the assays performed, classes A1–A6 covering Avian reactors and classes B1–B8 covering Bovine reactors. Where an animal has a high level of Avian reactivity (e.g. >A3) or a low level of Bovine reactivity (e.g. >B1) it is generally regarded as being of equivocal infective status. For such animals, a second blood sample is obtained and assayed which allows the animal to be diagnosed as either clear or infected.

In a further aspect the invention also relates to a method of differentiating between infection and immunity in a ruminant.

In this aspect, a first blood sample is obtained from the ruminant and the infective status is determined in accordance with the method described above. If, as a result of this, the ruminant is diagnosed as being infected, a second blood sample is taken after a period of time has elapsed which is sufficient to allow a determination as to whether the infection is becoming established or resolved to be made.

In order to achieve this, the assays, measurements and comparisons of steps (b), (c) and (d) of the method are performed as set out above and the infective status determined from the analysis of the second sample of blood is compared to that determined from the first sample of blood. Where the infection has become established, the results obtained from the second sample will place the ruminant in the category covering the relative rank of animals due for slaughter. In contrast, where the ruminant has developed an immunity to the infection and the infection has therefore become resolved, the results from the second sample will have moved downwards towards the reference distribution range determined for healthy animals. This is a particularly important advantage of the present method as it allows animals which would otherwise be slaughtered to be salvaged, thus avoiding unnecessary losses in terms of both breeding stock and capital.

Where the difference between the first infective status and the second infective status shows that the infection is becoming resolved, one or more additional samples may also be taken to monitor the resolution of the infection.

In this aspect of the invention, it is advantageous to allow a period of at least one month to pass between the samples. Preferably this period is between 3 and 6 months. Optimally, the period between the samples is as long as practicable considering the initial classification of the animal.

The in vitro method according to the invention offers a number of advantages over the in vivo skin testing method. These advantages include that of flexibility in that selected assays can be used to measure individual T-cell function; the advantage of specificity in that responses to closely related antigens (*M.bovis* and *M.avium*) can be distinguished within an assay; the advantage of sensitivity in that as laboratory assays can be carried out under highly controlled conditions, monitoring responses of certain cell sub-populations provides more definitive responses to discriminate between "resistant" and "infected" animals, and the advantage of repeatability in that multiple repeat tests can be carried out over a short time span without interference due to prior testing.

The application of the methods of the invention will now be illustrated by reference to a series of examples.

In vitro assays to determine the level of cellular immunity and inflammation were carried out using blood samples obtained from skin test reactor and control deer. The assay used in the examples was the LT assay which was performed as follows.

A sample of approximately 20mls of blood was obtained from each animal. Leukocyte cultures were obtained from the samples by the following procedure. The blood cells were separated on a buoyancy gradient and, after washing in culture medium (RPMI), resuspended in reference serum enriched culture medium at a standard concentration.

The leukocyte cultures thus obtained were tested using conventional preparations of tuberculin PPD of bovine, avian or human origin and johnin PPD, all obtained from CSL. Positive control transformation assays were set up using non-specific stimulants (Pokeweed mitogen-PWM and Concanavalin A - Con A) to verify the viability of each cell preparation. Negative controls were set up using leukocytes cultured in the absence of any stimulant.

100 $\mu$l of the leukocyte cells were then dispensed in triplicate into sterile micro culture wells. 50 $\mu$l of appropriate antigen, reference mitogen or control culture medium was then added to the respective wells. The cells were then incubated in a humidified $CO_2$ incubator for five days.

50 $\mu$l of a medium containing 0.5 $\mu$ Ci of a radiolabel ($^3$H-thymidine) was added to each well. The contents of each well were then harvested on to glass fibre discs prior to drying and counting in a $\beta$-scintillation counter. The results were expressed as the level of radioactivity per triplicate culture in counts per minute (cpms) $\times 10^2$. Group means were obtained for each stimulant and relative reactivity was established by comparison with both the positive and negative control values.

The parameters of inflammation measured in the examples included cell counts of both macrophage and neutrophil populations as well as a determination of both the plasma viscosity and of the level of fibrinogen in the sample. These measurements were performed as follows.

The blood cell populations were counted by introducing a 3ml sample into the automated harvester. An aliquot was then extracted by the machine which monitored the appropriate cell populations after the addition of specific chemicals in a automated cycle. Data was then analysed by comparison with internal standards and then expressed as total numbers of cells per ml, or in terms of cell ratios in percentage values.

Plasma viscosity was measured by flowing 500 $\mu$l of through a Harkness Viscometer.

The amount of fibrinogen present was measured by adding 165 $\mu$l of thrombin to 165 $\mu$l of plasma and measuring the fibrin produced.

EXAMPLE 1:

An investigation was made of a 'problem herd' in which clinical TB had been diagnosed. The results from testing the 'problem herd' enabled a critical assessment of the correlation between skin test responses and lymphocyte reactivity to be made. This herd first had clinical TB diagnosed in an adult hind in Feb. 1984.

Herd testing began 10 Feb. 1985 and of 200 animals tested, 62 were reactors. All reactors were slaughtered. The second herd test (13 Jun. 1985); 127 animals, tested 30 reactors. Five reactor hinds were examined (15 Jul. 1985) at autopsy and for lymphocyte reactivity. The results of this are shown in Table 2. Four weaners found dead, (1 Aug. 1985) disclosed clinical TB lesions on autopsy. All these animals were skin test negative on last herd test (13 Jun. 1985). The third herd test began on 29 Aug. 1985, blood samples being obtained from each of these animals prior to CT. Of 66 animals tested, 15 reacted; 7/21 weaners, 7/20 2-year old hinds, and 1/25 adult hinds.

Results obtained from the weaners (Table 3) and hinds (Tables 4 and 5) were suggestive that exposure to TB was widespread in this herd, with a large number of animals being highly reactive to *Myco bovis*. As a test of validity, the seven reactor weaners and one animal (No. 0998-Table 3) which was skin test negative but highly reactive to TB in leukocyte culture were slaughtered. The findings confirmed our prediction that 6 of the reactor weaners would have lesions, and that No. G301 would not be infected though skin test positive, because it was negative in the laboratory assay. Based on our findings we predicted that No. 0998 would be a False(−) to the skin test and should harbour TB lesions.

TABLE 2

Comparison Between Reactivity in Lesion Positive Skin Test Reactor Adult Deer and Controls

|  | Animal No | Bovine | Avian | Control |
|---|---|---|---|---|
| Lesion Reactors | Y140 | 432 | 231 | 18 |
|  | Y101 | 381 | 160 | 7 |
|  | 018 | 268 | 276 | 3 |
|  | HBR | 740 | 266 | 15 |
| Non Lesion Reactor | Y3 | 6 | 4 | 1 |
| Negative Control | 0956 | 4 | 1 | 1 |
|  | 0975 | 6 | 5 | 1 |
|  | 0984 | 6 | 5 | 1 |
|  | HBC | 13 | 6 | 10 |

(Results cpms × 10²)

Note:
(a) Level of Lymphocyte Reactivity to Bovine Tuberculin (>200) in Lesion Reactors
(b) Bovine > Avian
(c) Low response in Non-Lesion Reactor Query False (+) Skin Test Reactor

TABLE 3

Transformation in Weaner Skin Test Reactors and Controls from *Myco bovis* infected herd.

| Animal No | Bovine | Avian | Control | Autopsy Status |
|---|---|---|---|---|
| *Skin Test Reactors* | | | | |
| 0995 | 60 | 15 | 8 | Lesions |
| P319 | 53 | 14 | 4 | Lesions |
| G302 | 86 | 14 | 28 | Lesions |
| G301 | 1 | 1 | 4 | *No visible lesions |
| G305 | 137 | 26 | 6 | Lesions |
| 0990 | 23 | 9 | 9 | Lesions |
| Y110 | 166 | 26 | 57 | Lesions |
| *Skin Test Negative* | | | | |
| G313 | 31 | 6 | 22 | Not applicable (NA) |
| P301 | 4 | 3 | 2 | NA |
| G316 | 1 | 8 | 3 | NA |
| G300 | 3 | 2 | 2 | NA |
| G312 | 25 | 14 | 9 | NA |
| G310 | 33 | 4 | 4 | NA |
| G309 | 4 | 2 | 4 | NA |
| 0999 | 2 | 3 | 4 | NA |
| P302 | 40 | 30 | 5 | NA |
| 0998 | 150 | 37 | 13 | + Lesions on Autopsy |
| 0994 | 69 | 9 | 8 | NA |

Note:
Elective Autopsy carried out on all skin test positive weaners and one (0998) SUSPICIOUS skin test negative animal
1. * False (+) Reactor + False (−) Reactor
2. Reasonable correlation between skin test reactor status and lymphocyte transformation
3. Range 1-160 for Bovine Stimulation

TABLE 4

Transformation in Two-Year Old Hinds from *Myco bovis* Infected Herd

| Reactors | | | | Control | | | |
|---|---|---|---|---|---|---|---|
| Animal No | Bovine | Avian | Control | Animal No | Bovine | Avian | Control |
| 0980 | 124 | 57 | 53 | 0982 | 127 | 61 | 23 |
| 0972 | 270 | 61 | 18 | 0968 | 7 | 35 | 18 |
| 0970 | 9 | 19 | 8 | 0957 | 5 | 6 | 6 |
| 0984 | 86 | 12 | 5 | 0960 | 75 | 19 | 13 |
| 0985 | 235 | 59 | 43 | 0975 | 84 | 20 | 8 |
| 0965 | 86 | 46 | 83 | 0958 | 2 | 3 | 2 |
| 0986 | 42 | 19 | 3 | 0956 | 174 | 105 | 3 |
|  |  |  |  | 0963 | 218 | 63 | 20 |
|  |  |  |  | 0988 | 118 | 94 | 11 |
|  |  |  |  | 0976 | 32 | 25 | 19 |
|  |  |  |  | 0959 | 10 | 5 | 2 |
|  |  |  |  | 0978 | 13 | 17 | 14 |
|  |  |  |  | 0966 | 4 | 6 | 7 |

Note:
1. Prediction 0970 False (+) 0982, 0960, 0975, 0956, 0963, 0988, 0976 False (−)
2. *Myco bovis* implicated by Bovine > Avian Lymphocyte Response
3. Reasonable correlation between skin test reactivity and lymphocyte transformation

TABLE 5

Transformation in Adult Hinds from *Myco bovis* infected herd (*1/25 Animals was a skin test reactor)

| Animal No | Bovine | Avian | Control |
|---|---|---|---|
| *Y108 | 470 | 339 | 7 |
| Y46 | 39 | 11 | 30 |
| Y130 | 81 | 43 | 9 |
| RB | 321 | 117 | 17 |
| Y40 | 19 | 16 | 10 |
| Y2 | 257 | 189 | 30 |
| Y38 | 190 | 606 | 84 |
| Y93 | 153 | 148 | 31 |
| R11 | 61 | 37 | 5 |
| Y121 | 194 | 559 | 21 |
| Y104 | 467 | 288 | 10 |
| Y128 | 14 | 30 | 15 |
| Y197 | 28 | 190 | 5 |
| Y115 | 177 | 123 | 32 |
| Y109 | 40 | 46 | 22 |
| Y88 | 32 | 46 | 20 |
| Y113 | 165 | 99 | 11 |
| R84 | 101 | 52 | 13 |
| Y111 | 501 | 290 | 44 |
| Y105 | 460 | 356 | 11 |
| Y89 | 378 | 283 | 18 |
| Y199 | 257 | 241 | 145 |
| Y60 | 144 | 346 | 20 |
| Y94 | 192 | 129 | 28 |

Note:
1. Abysmal correlation between skin test status and lymphocyte transformation
2. Culture reactivity suggest only 1/25 (Y40) is above suspicion We were vindicated by confirming that this animal had lesions (retropharyingeal and mesenteric). Our results would also infer that a number of False(−) animals remain within the weaner group (5 out of 10). Based on these findings we would also predict that there are a significant number of False(−) animals in the 2 year old group (7 out of 13, Table 4) and adult group (16 out of 24, Table 5). All of these animals failed to respond to the 3 recently completed skin tests. The increasing level of reactivity in older animals is also striking, and suggests a high incidence of exposure to TB over a long period of time.

EXAMPLE 2:

This example compared the relative predictability of both the method of the present invention and the CT test to define lesion status in animals. The results of this test are shown in Table 6.

As can be seen from Table 6, the skin test identified as reactors five animals who on autopsy proved to have no lesions, while identifying as negative reactors five animals who in fact had lesions on autopsy. These results when converted to percentages show that the skin test had a 15% error in predicting both false (+) and false (−) animals.

In contrast, using the method of the present invention each of the animals predicted to have lesions in fact had lesions on autopsy. The method did however, identify one animal as having tuberculosis where no lesions were revealed on autopsy.

EXAMPLE 3:

TABLE 6

Predictability of Laboratory Test to Define Lesion Status of Animals.

| Animal No. | Blood Tests | | | | Skin Test | |
|---|---|---|---|---|---|---|
| | August 1985 | | Pre-Autopsy 1986 | | | |
| | Bovine | Avian | Bovine | Avian | Pre-autopsy | Lesions |
| P301 | 1 | 2 | 48 | 35 | —* | 4 |
| G316 | 1 | 8 | 369 | 268 | + | 6 |
| G300 | 2 | 2 | 361 | 125 | + | 4 |
| G309 | 5 | 3 | 151 | 32 | + | 4 |
| P302 | 2 | 4 | 83 | 36 | + | 4 |
| 0999 | 2 | 3 | 431 | 222 | + | 4 |
| 0994 | 69 | 9 | — | — | —* | 2 |
| 0998 | 150 | 36 | — | — | —* | 4 |
| 0995 | 60 | 15 | — | — | + | 4 |
| P319 | 53 | 14 | — | — | + | 4 |
| G302 | 86 | 14 | — | — | + | 3 |
| G305 | 137 | 26 | — | — | + | 2 |
| Y110 | 166 | 26 | — | — | + | 4 |
| P307 | — | — | 267 | 40 | + | 2 |
| P311 | — | — | 296 | 66 | + | 3 |
| G310 | 1 | 3 | 8 | 7 | — | 0 |
| G313 | 2 | 1 | 4 | 2 | — | 0 |
| G301 | 1 | 1 | 1 | — | +* | 0 |
| RB | 32 | 117 | 326 | 366 | —* | 6 |
| Y104 | 467 | 288 | 223 | 125 | + | 4 |
| Y89 | 377 | 283 | 661 | 487 | + | 3 |
| Y108 | 470 | 339 | 695 | 519 | + | 4 |
| Y105 | 460 | 356 | 488 | 232 | + | 6 |
| R11 | 61 | 37 | 321 | 85 | + | 3 |
| Y2 | 257 | 189 | 448 | 162 | + | 6 |
| Y94 | 192 | 129 | 46 | 28 | +* | 0 |
| Y38 | 190 | 606 | 25 | 292 | +* | 0 |
| Y88 | 32 | 46 | 84 | 66= | +* | 0 |
| R84 | 102 | 52 | 79 | 59 | —* | 3 |
| Y199 | 251 | 241 | 32 | 20 | +* | 0 |
| Y111 | 500 | 290 | 112 | 60 | — | 1 |
| Y115 | 177 | 123 | 22 | 10 | — | 0 |
| Y130 | 81 | 43 | 51 | 43 | — | 0 |
| Y93 | 153 | 148 | 22 | 132 | — | 0 |

TABLE 6-continued

Predictability of Laboratory Test to Define Lesion Status of Animals.

| | Skin Test* | Blood Test ± |
|---|---|---|
| False (−) | 5/34 (15%) | 0/34 (0%) |
| False (+) | 5/34 (15%) | 1/34 (3%) |

False (−) skin test Reactors disastrous in attempts to control T.B.
False (+) - cause wastage which is unnecessary and expensive
+ Lesion Classification 0 - Negative 1 Minimal → 6 Maximal Lesion This example demonstrates the ability of the method of the present invention to classify animals as either "clear", "immune" or "infected". The results of this investigation are summarised in Table 7.

From this table it can be seen that a significant number of the animals which were initially infected developed immunity and resolved the infection. This resolution was shown on autopsy where the animals which had been infected but had developed immunity were found to have no lesions.

This is a significant advantage of the present invention in that it would allow 57 "infected" animals to be salvaged and returned to the herd. Further, these animals having developed immunity to the infection are of very high value to the farmer.

EXAMPLE 4:

This investigation was designed to demonstrate the ability of the method according to the invention to discriminate between sensitization due to M.bovis as against M.avian in skin test reactors. The results are shown in Table 8.

All of the animals tested reacted positively to the CT test. However, when the method according to the invention is applied, it can be seen that all 12 animals in herd A are Avian reactors and therefore free from infection. These animals can therefore be salvaged.

This conclusion was confirmed upon autopsy where no lesions were found in any of the animals in herd A.

The data for herd B in contrast showed that all of the animals with the exception of animal 11 were Bovine reactors.

TABLE 7

The ability of Testing Systems to Define 'Clear', 'Immune' or 'Infected' Status of Test Animals

| | Status at Day 0 | Status at Day > 90≠ | Autopsy Findings | Infectious Status |
|---|---|---|---|---|
| (a) | N (73)* | N | No Lesions | CLEAR - UNINFECTED |
| (b) | B1 (20) | >B2 | Lesions (Grade 2-6) | INFECTION UNRESOLVED |
| (c) | B1 (42) | N | No Lesions | CLEAR - PRIOR Tb EXPOSURE; NO INFECTION ESTABLISHED |
| (d) | >B3 (15) | <B1 | No Lesions or Calcified Lesions | CLEAR - IMMUNE TO Tb |
| (e) | >B3 (18) | >B3 | Lesions (Grade 3-6) | INFECTION UNRESOLVED (SERIOUSLY AFFECTED ANIMALS) |

*Figures in Bracket = No of Test Animals
The Conventional Skin Test does not have the ability to make any definition of CLEAR vs IMMUNE vs INFECTED
False Results in Skin Testing of above groups results in:- (a) Loss of Uninfected animals (b) & (e) Inability to manage spread of infection, breakdown in control (c) & (d) Loss of 'ELITE' IMMUNE animals
≠Repeat samples taken at 3 month intervals

TABLE 8

Ability of Blood Assay to Discriminate between M-Bovis vs M-avium in Skin Test Reactors

| *Herd A | Blood Test Reaction Bovine | Avian | Autopsy Lesions |
|---|---|---|---|
| 1 | 106 | 183 | 0 |
| 2 | 62 | 34 | 0 |
| 3 | 65 | 83 | 0 |
| 4 | 43 | 119 | 0 |
| 5 | 309 | 635 | 0 |
| 6 | 374 | 382 | 0 |
| 7 | 78 | 321 | 0 |
| 8 | 123 | 435 | 0 |
| 9 | 66 | 389 | 0 |
| 10 | 157 | 541 | 0 |
| 11 | 68 | 148 | 0 |
| 12 | 34 | 112 | 0 |

| ±Herd B | Bovine | Avian | |
|---|---|---|---|
| 1 | 379 | 264 | 4 |
| 2 | 221 | 101 | 4 |
| 3 | 305 | 146 | 4 |
| 4 | 185 | 207 | 2 |
| 5 | 297 | 182 | 2 |
| 6 | 185 | 123 | 6 |
| 7 | 80 | 38 | 2 |
| 8 | 392 | 253 | 4 |
| 9 | 203 | 166 | 2 |
| 10 | 285 | 146 | 0 |
| 11 | 126 | 195 | 0 |
| 12 | 230 | 134 | 4 |
| 13 | 160 | 28 | 2 |
| 14 | 24 | 5 | 2 |
| 15 | 480 | 262 | 4 |

NOTE:
*Herd A all avian Reactors - no lesions
±Herd B all bovine Reactors except No 11 which is avian reactor with no lesions
Blood Test would salvage all animals in Herd A and No 11 in the seriously infected Herd B
A single blood test suggests severe infection in Herd B extensive slaughter necessary

TABLE 9

Influence of Skin Test on Blood Test Response to Bovine Tb

| Animal No. | Pre Skin Test | 3 Day Post Skin Test |
|---|---|---|
| P311 | 55 (B1) | 72 (B1) |
| G309 | 308 (B4) | 407 (B5) |
| 0985 | 485 (B5) | 283 (B3) |
| 0980 | 122 (B2) | 138 (B2) |
| 0984 | 185 (B1) | 135 (B1) |
| Y108 | 307 (B4) | 185 (B2) |
| Y104 | 267 (B3) | 286 (B3) |
| 0988 | 266 (B3) | 183 (B2) |
| Y2 | 248 (B3) | 287 (B3) |
| Y=30 | 101 (B1) | 156 (B1) |
| R== | 291 (B3) | 344 (B4) |
| Y88 | 17 (B1) | 27 (B1) |
| Y38 | 20 (B1) | 37 (B1) |
| 0964 | 374 (B4) | 317 (B4) |
| RB | 325 (B4) | 388 (B4) |

NOTE:
No significant drop in blood test response at time of reading skin test, 3 days following application of skin test.
Blood test can be used in conjunction with skin testing to define true infectious status of skin test Reactor animals.

These results would indicate that all of the animals except for animal 11 should be slaughtered. Animal 11 can be salvaged.

These predictions were vindicated on autopsy with the exception of the prediction for animal 10 in which no lesions were found.

Overall, using the method of the present invention, 13 of the animals tested would be salvaged from slaughter and returned to the herd.

EXAMPLE 5:

This investigation was designed to show the influence of the CT skin test on the results obtained using the method according to the present invention. The results of this investigation are summarized in Table 9.

From the results, it can be clearly seen that there is no significant drop in the response recorded using the method of the present invention. This would indicate that the method of the present invention can be used in conjunction with CT testing without having to wait for the expiry of any set length of time. The method can therefore be applied immediately after the diagnosis of some animals designated as skin test positive in order to determine their true infective status.

EXAMPLE 6:

This example shows the results of a recent case study in relation to a group of animals all identified as being skin test positive.

In the herd of 172 positive reactor animals which were sampled and subjected to a single test in accordance with the present method. This test showed 105 of the animals as being clear of infection, 49 as being of equivocal status, and 18 animals being likely tuberculous.

A second blood test which would routinely be conducted one month after the first blood test would allow the group originally identified as being equivocal to be definitively divided into either the clear or tuberculous groups.

This particular case study emphasises the advantages of the present invention to the farmer in that in reliance upon the CT test, 172 animals would be slaughtered. In contrast, using the method according to the present invention more than 130 animals will return to the herd with the consequent huge savings in cost to the farmer.

Thus, in accordance with the present invention there is provided a method by which both infection and immunity can be identified with a high degree of accuracy. To date, a total of 361 animals which have been tested have subsequently been subjected to autopsy. Using the method of the invention it was predicted 123 of these animals would be tuberculous while 238 would have no lesions. Upon autopsy, it was shown that 118 animals were tuberculous and 226 were not. This represents in percentage terms a correct diagnosis of at least 95% in each case.

The animals which comprise the above totals were drawn from 18 herds. In 8 of these herds it was predicted the presence of tuberculous animals. Subsequent slaughter and autopsy of the animals has confirmed in each case that TB was present in the herds in which we predicted.

In contrast, upon autopsy in the herds in which no infection was indicated using the method of the invention no lesions were found. Accordingly, on a herd basis the predictions made using the present method have thus far been completely accurate.

The step of comparing the results obtained in the mononuclear cell assay and in the measurement of a parameter of inflammation with the database can be performed by establishing a composite picture showing the multivariate analyses involved. This composite picture can then be compared with the "normal" picture established by the database.

Figure 2:
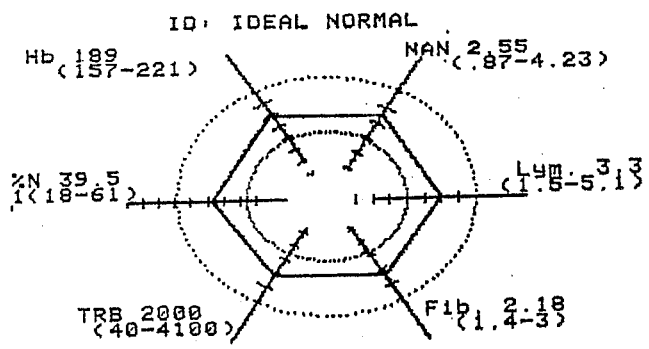
FIG. 2 is a multivariate analysis of immunological and inflammatory cell parameters.
Figure 2:
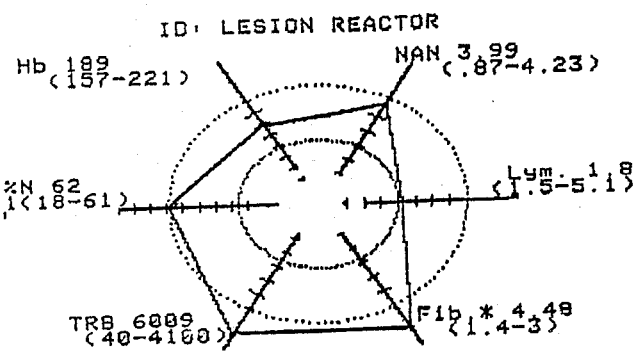
Figure 2:
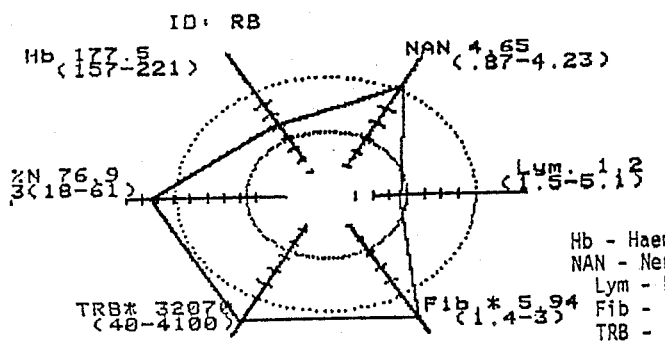

An example of such a composite picture is shown in FIG. 2. By combining haemotology, blood chemistry and leukocyte reactivity the distortion in the blood profile of lesion reactor animals (L) by comparison with the normal animal (N) established from the database can be seen. For an infected animal, the neutrophil count (NAN), percentage (%N), and fibrinogen (Fib) levels are elevated, while the lymphocyte (Lym) count is reduced. From this analysis, it can be seen that of the animals involved adult hind RB (Table 5) showed a classical "lesion reactor" profile although not reacting to the intradermal CT test. The prediction was therefore that this animal showed likely false (−) reactor response and harbours TB. The haematological parameters in many of the remaining adults (10 out of 24) were also compatible with TB lesions.

Adult hind RB was felt to be of particular interest in that this animal had consistently responded negatively to the CT test. This animal was then tested on three more occasions over a period covering approximately 8 months in order to provide a series of composite pictures. This series is shown in FIG. 3.

Figure 3:
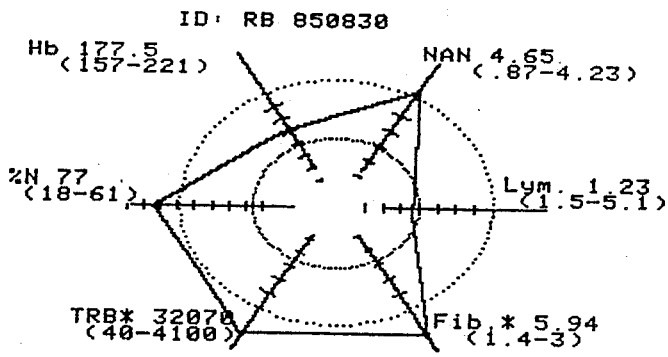
FIG. 3 shows a series of multivariate analyses taken from one infected animal over an eight month period.
Figure 3:
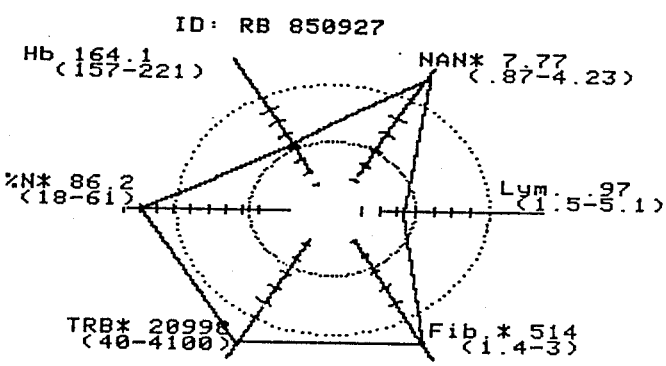
Figure 3:
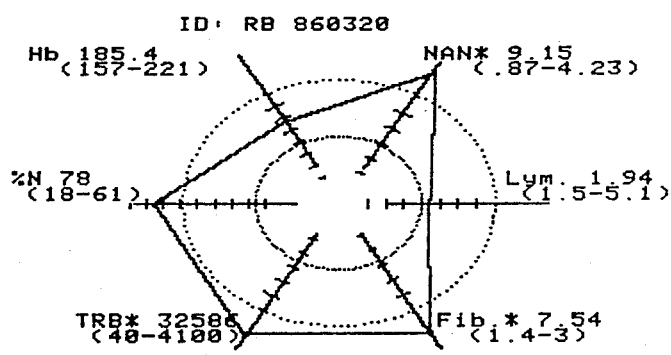

From FIG. 3 it can be seen that adult hind RB showed a consistent distortion in terms of blood profile from what would be predicted for a normal non-infected animal. At the same time as the tests in accordance with the present invention were performed, hind RB was also tested using the conventional CT test. All of the CT tests showed negative reactivity.

Upon autopsy, adult hind RB was found to have one of the worst cases of TB infection found. She had however responded negatively to the CT test on 14 consecutive occasions.

Thus, in accordance with the present invention there is provided a method of both detecting infection and immunity in ruminants which provides significant advantages over those methods presently used. The present invention therefore adds a new dimension to the diagnosis of infection in ruminants.

The particular advantages of the invention become apparent when the use of the method to diagnose TB in deer is compared to existing methods.

Firstly, the data obtained from blood culture in Tables 2-5 shows that the present method has real value in specialised application in certain herds. The data obtained from the weaners (Table 3) was used to predict the status of 8 weaners (7 reactors and 1 skin test negative), and it allowed
  (a) To confirm lesion reactor status in 6 animals;
  (b) To exclude False(+) Myco bovis reactors (1 animal); and
  (c) To identify False(−) Myco bovis reactors (1 animal).

The overall accuracy of the method of the present invention as compared to the CT test is also clearly shown by reference to Table 6 where the CT test inaccurately predicted the status of 10 animals while the present method was incorrect on one occasion only.

A further and most important advantage of the present method lies in its ability to distinguish between "clear", "immune" and "infected" status amongst animals, in a tuberculous herd, which have reacted positively to the CT test. On the basis of the tests performed thus far, a significant proportion of the positive reactors can be returned to the herd as either clear or immune. The benefits of this capability to the farmer in terms of minimising stock loss and consequently capital loss will be readily apparent.

The ability of the method of the invention to distinguish between infected and immune animals also has a great impact on the management of an infected herd. After the initial infective status of the animals has been determined by the testing of the first sample, the three groups of animals can be separated to ensure that the infection is contained. After the second blood sample is taken and tested for the equivocal and infected groups, it can be determined whether the animals in these groups are in fact still infected or whether the infection has been resolved. The animals in which the infection has been resolved can then be returned to the herd whereas the animals in which the infection has become established can be culled.

Further consequences of using the method of the invention insofar as farm management is concerned can again be seen by reference to Tables 2-5. The pattern of reactivity and disease susceptibility emerging within the "problem herd" suggest that certain groups are particularly prone to produce False(−) skin test reactions (weaners infected neonatally and pregnant hinds). This allows an adjustment to management techniques to be made in order to isolate the high risk categories from the remaining non-infected animals as a safeguard. In addition classification as regards risk would allow a farmer to make an objective evaluation of all animals of reactor status within his herd. The risk factor could then be balanced against the possible benefits in retaining an animal should subsequent testing prove it to be clear of infection.

An additional advantage of the present method lies in its ability to discriminate between atypical *M.avium* sensitization and true *M.bovis* infection. At present, positive reactions to the CT test may occur in a herd due to *M.avium* sensitization. In the current situation, this could lead to the culling of animals from a herd in which there is no TB infection.

Lastly, the method of the invention has the advantage of repeatability. The CT test used at present cannot be repeated upon the same animal for a period of approximately 3 months. In contrast, the method of the present invention can be performed immediately after the CT test in order to check the accuracy of the evaluation made.

The present invention provides a method of detecting infection and immunity and ruminants which is of general application. Although the invention has been particularly described in relation to the detection of TB in deer, it will be appreciated by those persons skilled in the art that the methods involved can easily be applied to other diseases and ruminants.

Initial investigations with a small number of blood samples from cattle indicate that the method of the invention can easily and simply be applied to detect infection (for example TB) in bovines. The results of these investigations are shown in Table 10.

TABLE 10

| | Leukocyte Reactivity in Six Tb Reactor Bovines (All had lesions at Post Mortem) | | | |
|---|---|---|---|---|
| Animal No | Avian Reactivity | Bovine Reactivity | Positive Control | Negative Control |
| 1R | *5(3)+ | 32(11) | 73(125) | 4(1) |
| 2R | 3(2) | 87(54) | 68(146) | 2(4) |
| 3R | 4(2) | 34(16) | 56(138) | 2(4) |
| 4R | 10(2) | 73(36) | 64(114) | 4(2) |
| 5R | 8(3) | 70(17) | 66(129) | 4(4) |
| 6R | 6(4) | 80(36) | 121(148) | 3(3) |

*Purified Leukocyte
+Whole Blood Cultures

TABLE 2

| | | Controls Tb Free | | |
|---|---|---|---|---|
| 1 | *2(1)+ | 2(1) | 80(122) | 2(1) |
| 2 | 3(2) | 2(2) | 117(148) | 2(2) |
| 3 | 1(1) | 1(1) | 87(126) | 1(1) |
| 4 | 2(3) | 2(2) | 64(137) | 3(3) |
| 5 | 2(3) | 2(4) | 79(94) | 3(4) |
| 6 | 2(2) | 1(2) | 56(90) | 2(3) |

All results given as counts per minute × $10^3$

In practice, the data shown above in Table 10 would be combined with measurements of parameters of inflammation and compared with a database established in accordance with the guidelines set out earlier in order to determine the infective status of the animals. However, even at this initial stage it seems clear that infection is generally indicated where Bovine reactivity exceeds Avian reactivity by a factor of at least 2.

Those persons skilled in the art will understand that the invention is not limited to the embodiments described above but only by the appended claims.

What is claimed is:

1. A method of detecting infection in a ruminant, said method comprising the steps of:
   (a) obtaining a sample of blood from said ruminant;
   (b) conducting an assay of mononuclear cell function;
   (c) measuring a parameter of inflammation of the ruminant from the blood in said sample; and
   (d) comparing the results obtained in steps (b) and (c) with a predetermined database to establish the infective status of said ruminant.

2. A method according to claim 1 wherein the assay conducted in the step (b) tests for the transformation of T-cells or for lymphokines produced by activated T-cells.

3. A method according to claim 2 wherein the lymphokines tested for are interleukin-2, Pro-coagulant, interferon or tumor necrosis factor.

4. A method according to claim 1 wherein the parameter of inflammation measured for is a macrophage cell count, a neutrophil cell count, the plasma viscosity of the sample or the level of inflammatory plasma proteins in the sample.

5. A method according to claim 4 wherein the inflammatory plasma proteins measured for are fibrinogen or α-2 globulins.

6. A method of differentiating between infection and immunity in a ruminant, said method comprising the steps of:
   (a) obtaining a first sample of blood from said ruminant;
   (b) conducting an assay of mononuclear cell function in said first sample;
   (c) measuring a parameter of inflammation of the ruminant from the blood in said first sample;
   (d) comparing those results obtained in steps (b) and (c) with a predetermined database to determine a presumptive diagnosis of the infective status of said ruminant;
   (e) if the presumptive diagnosis suggests that the ruminant is infected, waiting for a period of time to elapse which is sufficient to allow for confirmation to be made as to whether the infection is becoming established or resolved;
   (f) obtaining a second sample of blood from said ruminant;
   (g) repeating steps (b), (c) and (d) for said second sample in order to determine a confirmatory diagnosis of the infective status of said ruminant; and
   (h) comparing the presumptive first infective status and the confirmatory infective status in order to determine whether said infection is becoming established or resolved.

7. A method according to claim 6 further including repeating steps (b)–(d) for a third sample where the infection is becoming resolved in order to monitor the resolution of the infection.

8. A method according to either claim 6 wherein the period of time between each sample is at least one month.

9. A method according to claim 8 wherein the period of time between each sample is from 3 to 6 months.

10. A method according to claim 1 wherein more than one parameter of inflammation is measured.

11. A method according to claim 1 wherein the infection is tuberculosis.

12. A method according to claim 1 wherein the ruminant is a deer.

13. A method according to claim 12, wherein the predetermined database for deer is as follows:

| CONTROL ANIMAL REFERENCE VALUES | | | |
|---|---|---|---|
| Avian PPD | Bovine PPD | Concanavalin A | Control |
| Mean 450* | 516 | 63,456 | 360 |
| Standard Deviation 135 | 203 | 20,154 | 163 |

*Cpms.

| Cut Points for Classification | |
|---|---|
| Avian Reactor Transformation (Range 10–675)+ | Bovine Reactor Transformation (Range 10–774) |
| A1 10–100 | B1 10–100 |
| A2 101–200 | B2 101–200 |
| A3 201–300 | B3 201–300 |
| A4 301–400 | B4 301–400 |
| A5 401–500 | B5 401–500 |
| A6 501–600 | B6 501–600 |
| A7 601–700 | B7 601–700 |
| | B8 701–800 |

+Cpms. × $10^2$

Haematology Range (Weaners)

| | | | | |
|---|---|---|---|---|
| Fibrogen | 167–387 | (mg/dL) | Neutrophils | 26–65% |
| Plasma viscosity | 1003–1171 | (cp) | Neutrophils | 0.79–4.21 × $10^9$/L |
| Haemoglobin | 160–213 | (g/L) | Lymphocytes | 1.34–3.61 × $10^9$/L | results being expressed as counts per minute (Cpms) following incubation of $2 \times 10^5$ deer mononuclear cells with 0.5 μ Ci 3H-thymidine for the last 18 hours of a 144 hour culture period, reference range, means and standard deviations being derived from 205 mixed age adult deer taken from Tb free properties without a history of skin test reactions, reactor range being taken from 145 Avian Reactor and 450 Bovine Reactor samples.

* * * * *